United States Patent [19]

Papenfuhs et al.

[11] 4,443,630
[45] Apr. 17, 1984

[54] PROCESS FOR PREPARING 2-AMINO-5-NITROTOLUENE

[75] Inventors: Theodor Papenfuhs, Frankfurt am Main; Rüdiger Berthold, Bad Soden am Taunus, both of Fed. Rep. of Germany

[73] Assignee: Hoechst Aktiengesellschaft, Fed. Rep. of Germany

[21] Appl. No.: 453,510

[22] Filed: Dec. 27, 1982

[30] Foreign Application Priority Data

Jan. 8, 1982 [DE] Fed. Rep. of Germany ....... 3200308

[51] Int. Cl.$^3$ ............................................ C07C 85/04
[52] U.S. Cl. .................................................... 564/406
[58] Field of Search ......................................... 564/406

[56] References Cited

U.S. PATENT DOCUMENTS 3,277,175 10/1966 Clemens .............................. 564/406
3,313,854 4/1967 Levy .................................... 564/406
4,122,118 10/1978 George et al. ...................... 564/406

Primary Examiner—Paul F. Shaver
Attorney, Agent, or Firm—Connolly & Hutz

[57] ABSTRACT

2-Amino-5-nitrotoluene is obtained in high yield by reacting 2-chloro-5-nitrotoluene with excess aqueous ammonia which has a concentration of at least 30% by weight. The product is used as a diazo component for preparing azo compounds.

10 Claims, No Drawings

PROCESS FOR PREPARING 2-AMINO-5-NITROTOLUENE

2-Amino-5-nitrotoluene serves as a valuable diazo component for preparing azo compounds, for example water-insoluble azo dyestuffs on the fiber by the ice-color technique.

The so far single industrially feasible synthesis is described by BIOS Final Report 986/2, No. 167, pages 297–306, and involves acylating 2-aminotoluene with benzenesulfonyl chloride to give N-(2-methylphenyl)-benzenesulfonamide, nitrating the latter in chlorobenzene, and, finally, splitting off the protective group by hydrolysis and isolating 2-amino-5-nitrotoluene. This synthesis gives a yield of about 75% of theory. In addition to this unsatisfactory yield, the numerous process stages and the associated consumption of chemicals, this process harbors further grave disadvantages which render its industrial application problematical from a processing and an ecological point of veiw The nitration in a solvent requires high expenditure on safety precautions, since ignitable gas mixtures can form. Also, separate special units are required for the necessary solvent regeneration.

The hydrolytic elimination of the protective group, with the formation of benzesulfonic acid, can only be effected by means of a great excess of concentrated sulfuric acid, from which the 2-amino-5-nitrotoluene desired is isolated by filtration. Apart from the fact that considerable plant investment is necessary to separate the product from sulfuric acid, this step results in an acidic filtrate which is highly polluted with organic matter, since the entire benzenesulfonic acid remains dissolved in the sulfuric acid used in excess and cannot be regenerated. The filtrate can only be disposed of by burning in an acidproof plant, since it is not biologically degradable due to the high organic and inorganic load.

There existed therefore a demand for a process for preparing 2-amino-5-nitrotoluene which substantially avoids the disadvantages discussed and can be carried out in an industrially and ecologically favorable manner to give high yields.

It has now been found that 2-amino-5-nitrotoluene can be prepared in almost quantitative yield by reacting 2-chloro-5-nitrotoluene with aqueous ammonia which has a concentration of 30% by weight.

The reaction proceeds at an adequate rate at temperatures from about 180° C. upwards. Temperatures above about 250° C. are less favorable due to the pressures which arise. A reaction temperature of 200°–220° C. is preferable. Catalytic amounts of copper or of copper compounds can be added to accelerate the reaction or rather lower the reaction temperature. The ammonia is used in excess. Unreacted ammonia can be returned into the process. The by-product formed in this reaction is merely 1 mole of ammonium chloride. The concentration of the ammonia used is advantageously up to 80, preferably 40 to 70, % by weight. The reaction can be carried out discontinuously or continuously. The prevailing pressures of 60–100 bar can favor a continuous reaction, for example in externally heated tube reactors, by virtue of the smaller need for space and hence equipment.

2-Chloro-5-nitrotoluene, which is required as a starting product, is accessible by nitrating o-chlorotoluene (Rec. Trav. Chim. Pays-Bas 32, (1913) 244 et seq.). It can be isolated from the resulting mixture of isomers by distillation in 43% yield (Loc. cit. 286). This distillation gives pure 2-chloro-6-nitrotoluene as first runnings the other isomers can be separated in a known way. Since all isomers, by virtue of their reactive groups, are intermediates which can be put to many uses and for which there is adequate demand, no undesirable by-products are obtained in this reaction. Thus, even if this preliminary stage is included, this invention represents a very favorable procedure.

The process according to the invention thus enables 2-amino-5-nitrotoluene to be prepared in a significantly simpler way than in the existing process, not producing any undesirable by-products. The quality of the product enables it to be used whithout further purification for preparing azo compounds.

In the examples which follow, the percentage data are percentages by weight, unless otherwise stated.

EXAMPLE 1

In a 1 Liter steel autoclave, a mixture of 86 g of 2-chloro-5-nitrotoluene, 300 g of 25% aqueous ammonia solution, 1 g of basic copper carbonate and 100 g of liquid ammonia were heated at 200° C. for 12 hours with efficient stirring. During this period, a pressure of 90 bar built up. The batch was then cooled down to room temperature, and excess ammonia was blown off. The reaction solution was then filtered with suction. The residue obtained was 71.5 g of 2-amino-5-nitrotoluene, which was dried in a vacuum drying cabinet at 60° C. The yield was 68.4 g, which corresponds to 90% of theory; melting point: 118°–122° C. According to analysis by gas chromatography, the product contained 98.7 to 99.8% of 2-amino-5-nitrotoluene, no 2-chloro-5-nitrotoluene (starting product) and only 0.2 to 1.3% of components which can be eluted later on.

EXAMPLE 2

172 g of 2-chloro-5-nitrotoluene were heated at 200° C. for 12 hours together with 300 g of 25% strength aqueous ammonia solution and 150 g of liquid ammonia. During this period a pressure of about 100 bar built up. When the autoclave had been cooled down to room temperature and its pressure released, the reaction mixture was filtered with suction. 78.5 g of moist product were obtained, giving, after drying in a vacuum drying cabinet at 60° C., 72.0 g of dry 2-amino-5-nitrotoluene (melting point: 120°–123° C.), which corresponds to 94.7% of theory. According to analysis by gas chromatography, the composition of this crude product corresponded to the composition indicated in Example 1.

We claim:

1. A process for preparing 2-amino-5-nitrotoluene, wherein 2-chloro-5-nitrotoluene is reacted with aqueous ammonia which has a concentration of at least 30% by weight.

2. The process as claimed in claim 1, wherein the reaction takes place at 180°–250° C.

3. The process as claimed in claim 2, wherein the reaction takes place at 200°–220° C.

4. The process as claimed in claim 1, wherein the concentration of the ammonia used is up to 80% by weight.

5. The process as claimed in claim 1, wherein the concentration of the ammonia used is 40 to 70% by weight.

6. The process as claimed in claim 2, wherein catalytic amounts of copper or of copper compounds are added along with the aqueous ammonia to permit a lower reaction temperature, and said ammonia is used in excess.

7. The process as claimed in claim 1, wherein the reaction is carried out continuously.

8. A process for preparing 2-amino-5-nitrotoluene, comprising the step of heating to at least 180° C. the reaction mixture consisting essentially of 2-chloro-5-nitrotoluene and aqueous ammonia, said aqueous ammonia having a concentration of at least 30% by weight, and recovering the 2-amino-5-nitrotoluene product essentially without purification steps.

9. A process according to claim 8, wherein liquid ammonia is added to said reaction mixture to maintain said concentration of at least 30% by weight.

10. A process according to claim 8, wherein the by-product of the process is essentially ammonium chloride.

* * * * *